(12) United States Patent
Thorne, Jr. et al.

(10) Patent No.: US 7,841,581 B2
(45) Date of Patent: Nov. 30, 2010

(54) NEEDLE-FREE MEDICAL CONNECTOR

(75) Inventors: Gale Harrison Thorne, Jr., Bountiful, UT (US); Gale Harrison Thorne, Bountiful, UT (US)

(73) Assignee: Thorne Consulting & Intellectual Property, LLC, Bountiful, UT (US)

( * ) Notice: Subject to any disclaimer, the term of this patent is extended or adjusted under 35 U.S.C. 154(b) by 338 days.

(21) Appl. No.: 12/151,192

(22) Filed: May 5, 2008

(65) Prior Publication Data

US 2009/0057589 A1    Mar. 5, 2009

(51) Int. Cl.
  *F16L 37/28*   (2006.01)
(52) U.S. Cl. .................. 251/149.7; 251/149.6; 604/249
(58) Field of Classification Search .................. 251/149, 251/149.1, 149.3, 149.6, 149.7; 604/249, 604/259, 905, 183, 167
See application file for complete search history.

(56) References Cited

U.S. PATENT DOCUMENTS

| | | | |
|---|---|---|---|
| 4,143,853 A | 3/1979 | Abramson | |
| 5,006,114 A | 4/1991 | Rogers et al. | |
| 5,242,432 A | 9/1993 | DeFrank | |
| 5,423,791 A | 6/1995 | Bartlett | |
| 5,549,566 A * | 8/1996 | Elias et al. | 604/167.03 |
| 5,700,248 A * | 12/1997 | Lopez | 604/249 |
| 5,730,418 A | 3/1998 | Feith et al. | |
| 5,782,816 A | 7/1998 | Werschmidt et al. | |
| 5,901,942 A | 5/1999 | Lopez | |
| 5,947,954 A | 9/1999 | Bonaldo | |
| 6,758,833 B2 | 7/2004 | Lopez | |
| 6,875,205 B2 | 4/2005 | Leinsing | |
| RE39,334 E | 10/2006 | Lynn | |
| 7,160,272 B1 | 1/2007 | Eyal et al. | |
| 7,244,249 B2 | 7/2007 | Leinsing et al. | |

* cited by examiner

Primary Examiner—John K Fristoe, Jr.
(74) Attorney, Agent, or Firm—Gale H. Thorne (57) ABSTRACT

A needleless connector for controllably permitting fluid communication between a cannula and a port usually associated with a patient catheter or line. The connector is made from three parts, two of which form an elongated housing for a valve part. The valve part comprises a domed slit valve which is in a closed state before a cannula is inserted into the housing. Insertion of the cannula inverts the dome valve to open a slit permitting fluid communication there through. Insertion of the cannula also displaces the valve part about and along a post internally disposed in the housing. Assembled, the valve part is initially disposed about the post in a compressive sealed relationship to form a secure pathway therebetween. The post is shaped to store greater energy by stretching portions of the valve part as the valve part is displaced therealong. Upon removal of the cannula, stored energy is released from the stretched portion of the valve part to return the valve part to an original state, presenting a closed and cleanable surface to a user.

11 Claims, 5 Drawing Sheets

Figure 11

NEEDLE-FREE MEDICAL CONNECTOR

BACKGROUND

A variety of needle-free medical connectors are currently commercially available. Such connectors are generally used in handling and administering parenteral fluids, especially fluids associated with extension sets and patient catheters. These connectors are more specifically designed to interface, on a fluid dispensing and acquiring end, with a first, usually female, luer fitting, thereby to interface with fittings such as those commonly found on conventional syringes. On the other end, often, interface is through another luer fitting to provide a needleless communicating link to a catheter or an extension set affixed to a catheter.

An example of a needle-free connector is disclosed in U.S. Pat. No. 7,244,249 B2, titled NEEDLE-FREE MEDICAL CONNECTOR WITH EXPANDABLE VALVE MECHANISM AND METHOD OF FLUID FLOW CONTROL, issued Jul. 17, 2007 to Karl R. Leinsing, et al., and (Leinsing). Similar technology is also disclosed in U.S. Pat. Nos. 7,306,199, 7,184,825, 7,104,520, 6,706,022, 6,706,022, D468,016, 5,676,346 and 5,549,577. Leinsing discloses a needle-free connector having a two part housing and an associated piston element which is also made of two parts and contained within the housing. One of the piston element's parts is disposed within the other element part. The outer part has a compressible section which is compacted by insertion of a cannula into the housing and against the piston element to actuate a self-opening valve. The valve self-opens when the piston element is displaced from a state at a first position to a second position. Energy stored in the compressed section returns the piston element to the first position and valve closed resting state upon removal of the cannula which displaced the piston element part for such actuation.

Another example of a needle-free connector is disclosed in U.S. Pat. No. 5,901,942, titled MEDICAL VALVE, issued May 11, 1999 to George A. Lopez (Lopez). Lopez discloses a needleless valve device which utilizes a hollow spike having a closed tip to pierce a seal as the seal is forced across the tip by an ANSI tip of a medical implement. By so forcing the tip against the seal, the seal is displaced, permitting side holes within the tip to be open to fluid flow.

An example of a slit-valve free needleless connector is disclosed in U.S. Pat. No. 5,782,816, titled BIDIRECTIONAL VALVE AND METHOD OF USING SAME, issued Jul. 21, 1998 to Gary S. Werschmidt, et al. (Werschmidt). Werschmidt discloses a plug which is displaced within a housing by an inserted luer fitting to open access to a pathway there through. Of note is axial compression of the plug to a canted position to permit the access. Concern for such compressible plugs is possible reflux which may result when the plug is permitted to decompress when the luer fitting is removed and a lack of a closed seal about an inserted cannula tip.

Analysis of these approaches to needle-free design and general requirements of such connectors yields a number of important connector properties including needs for:

1. Inherently low manufacturing cost, making disposal after use efficacious.

2. Low dead space.

3. Ability to be sterilized before use to assure an initially uncontaminated product.

4. An accessible entry point for a cannula (e.g. a male luer fitting)

5. Facility for swabbing or otherwise cleaning the entry point to protect against contamination of fluids transferred through the connector.

6. Leak-free connection between a communicating cannula (e.g. a luer fitting of a syringe) and an associated valve component disposed as an integral part of each needle-free connector 7. A normally closed valve which is opened upon insertion of the cannula (e.g. a male syringe luer fitting) to permit bidirectional fluid flow through the connector and which is self-closing upon removal of the cannula or fitting.

8. Providing a positive pressure in residual fluid in the connector upon valve closure to obstruct retrograde (reflux) flow from a downstream positive pressure source upon valve closure 9. Internal pathways through the connector which are readily flushed to clear residual liquid from the connector as a result of a flush cycle, thereby reducing dangers associated, for example, with hazardous drug retention and incompatible drug mixing.

10. Capacity for retaining the cannula in place throughout a fluid transfer procedure.

11. Ability to securely interface with a female luer associated with communicating with a catheter or extension set (in at least one design).

BRIEF SUMMARY AND OBJECTS OF THE INVENTION

In brief summary, this novel invention of a needle-free connector exhibits all of the properties listed above. A needle-free connector housing according to the instant invention provides for controllably permitting fluid communication through a passageway disposed therein. The connector housing has an elongated hollow cylindrical shape which is formed by a first part affixed to a second part, the parts being securely affixed together about a medially disposed longitudinal axis. The first part is fitted with an externally communicating port being adapted to receive a blunt cannula. The second part has a port, oppositely disposed to the first port, which is adapted for communication from the passageway to a conduit externally affixed to the second port. Parts of the housing may be made from synthetic resinous material such as polypropylene or polycarbonate.

Internally disposed within the passageway of the housing is a displaceable valved component. The displaceable valved component has an externally facing valve disposed to be associated with the port of the first part, the valve being normally closed when the component is in a first position prior to being forcibly opened by contact and displacement by a blunt cannula Insertion of the blunt cannula into the first port effectively displaces the component toward a second position.

The second part has a hollow post which projects inwardly into the housing from the port of the second part. The hollow post has a medially disposed through hole which communicates with the port of the second part and has an external surface which generally decreases in radial dimension relative to the medical axis along the inward projection.

The displaceable valved component has a hollow elongated tubular body which is substantially rigid lengthwise but radially elastic and deformable, the body having a length which extends, in the first position, from said first port interface on one end to an elastically expandable portion on the opposite end. The component being sufficiently long to cause the elastically expandable portion to sealingly embrace a proximally disposed portion of the post with an associated force to assure that the passageway is closed and sealed when the component is in the first position. When the component is inwardly displaced by insertion of a blunt cannula, the expandable portion is further displaceably forced over the hollow post. Such displacement further elastically expands the expandable portion as it embraces a greater proximal portion of the post thereby storing potential energy within elastic memory of the elastically expandable portion.

It is important to note that selected materials of the external surface of the post and the associated portion of the elastically expanded body should have a coefficient of friction such that, in combination with radial force exerted by the elastically expanded portion of the body, the displaceable component is thereby stressed to be displaced from the second position to the first position when the blunt cannula is displaced from contact against the displaceable component. Such displacement is also disclosed in Thorne, Jr. (the U.S. Patent Application from which this Application for Patent continues-in-part).

Further, it is preferred that the valved component have a slit valve. It is also preferred that the structure of the valve be domed in shape. To enhance the lengthwise rigidity of the component, it is recommended that a plurality of thickened longitudinal ribs be disposed along the periphery of the component. Further, care should be taken to provide sufficient material, disposed between the ribs, to permit necessary and desired elastic expansion when displaced over the post. While other shapes may be used, a cone or frustrum shape is presently preferred for the post.

The component may be made from butyl rubber, a material which has elastic properties, but little permanent memory if stretched within the elastic limit of the material. In a preferred embodiment, the component has a substantially hollow cylindrical core. Along the path of displacement of the cylinder of the component, outwardly extending ribs of the component and internal structure of the body cooperate to flatten the cylindrical core in the first position and permit a full measure of expansion of the core in the second position. Thus, when the component is displaced toward the second position, internal volume within the component is increased. When the component is displaced toward the first position, the internal volume is significantly decreased. This increase and subsequent decrease in internal volume results in a positive liquid displacement as the cannula is retracted and a positive deterrent to reflux flow. To assure a necessary seal between the post and expandable portion, a plurality of radial ribs are preferably disposed on the inside of the expandable portion as disclosed in detail hereafter.

Two stops are provided within the housing and along the length of the component to assure proper operation. A first stop is disposed to limit displacement component toward the first port to retain the valved portion within first port at the first position. A second stop is disposed to limit component displacement about the post and thereby assure insertion of a cannula activates the slit valve to an open state.

Accordingly, it is a primary object to provide a needle-free connector which comprises not more than three moldable parts, has an inherently low manufacturing cost and acceptably low dead space.

It is an object to provide a connector which is able to be sterilized after assembly.

It is an important object to provide a port of the connector which is compatible with a conventional luer fitting (such as a syringe fitting) of a cannula.

It is a very important object to provide a connector having a first port external surface which is compatible with cleaning by swabbing or other accepted surface cleaning methods.

It is an object to provide an interface between a connector and an inserted cannula which affords a leak-free connection when the cannula is inserted into the first port to thereby displace the displaceable component.

It is an elementary object to provide a component having a self-closing valve which is opened upon displacement by force of insertion of the cannula and self-closes upon retraction of the cannula.

It is a consequential object to provide a flow path within the displaceable component which is greater in volume when the valve is open than when the valve is closed to assure resulting fluid pressures within the component which deter refluxive flow thereby.

It is also a consequential object to provide a flow path which is compatible with being cleared by flushing.

It is an object to provide facility for interfacing with a syringe luer fitting at a cannula receiving site.

It is another object to provide additional facility for interfacing with a communicating catheter or extension set at a site opposite the cannula receiving site.

These and other objects and features of the present invention will be apparent from the detailed description taken with reference to accompanying drawings.

DETAILED DESCRIPTION OF THE ILLUSTRATED EMBODIMENTS

In this description, the term proximal is used to indicate the segment of the device normally closest to the object of the sentence describing its position. The term distal refers to the other end. Reference is now made to the embodiments illustrated in FIGS. 1-12 wherein like numerals are used to designate like parts throughout. Primes of numbers refer to parts which are similar to parts having like numbers but are not identical with those parts in form or function.

Figure 1:
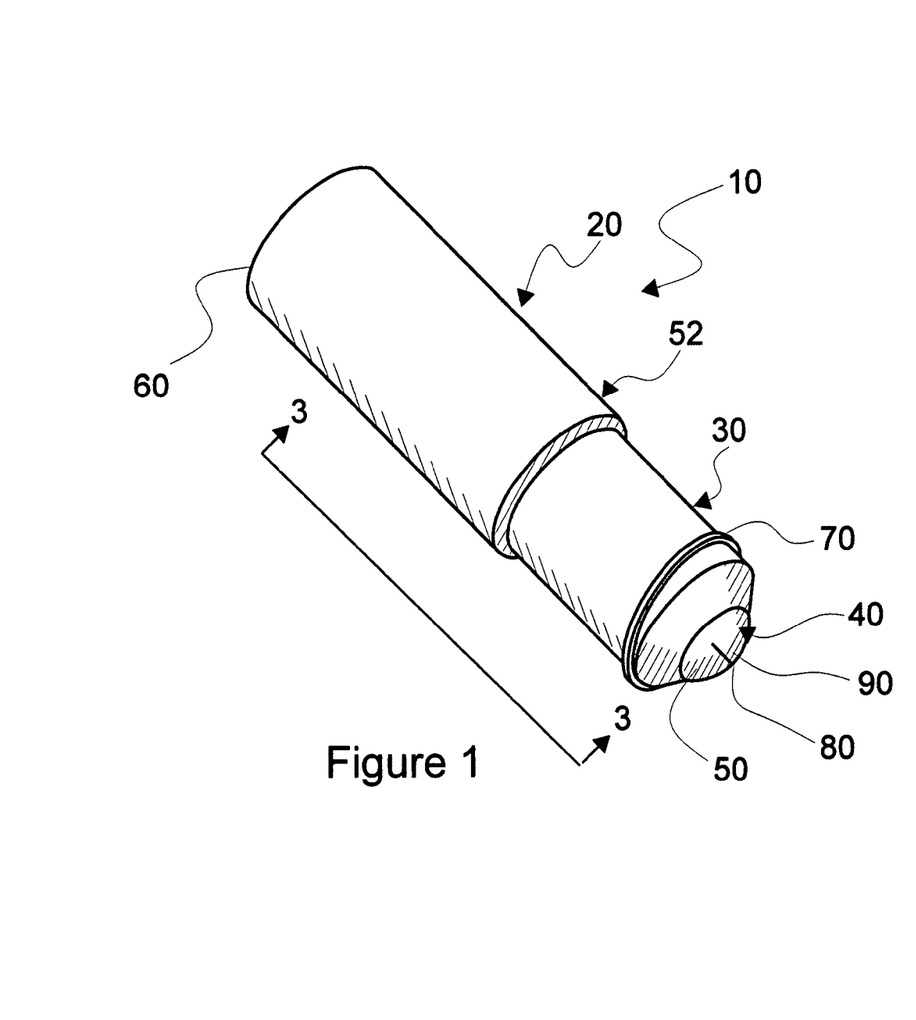
FIG. 1 is a perspective of a needle-free connector according to the present invention.
Figures 2, 8:
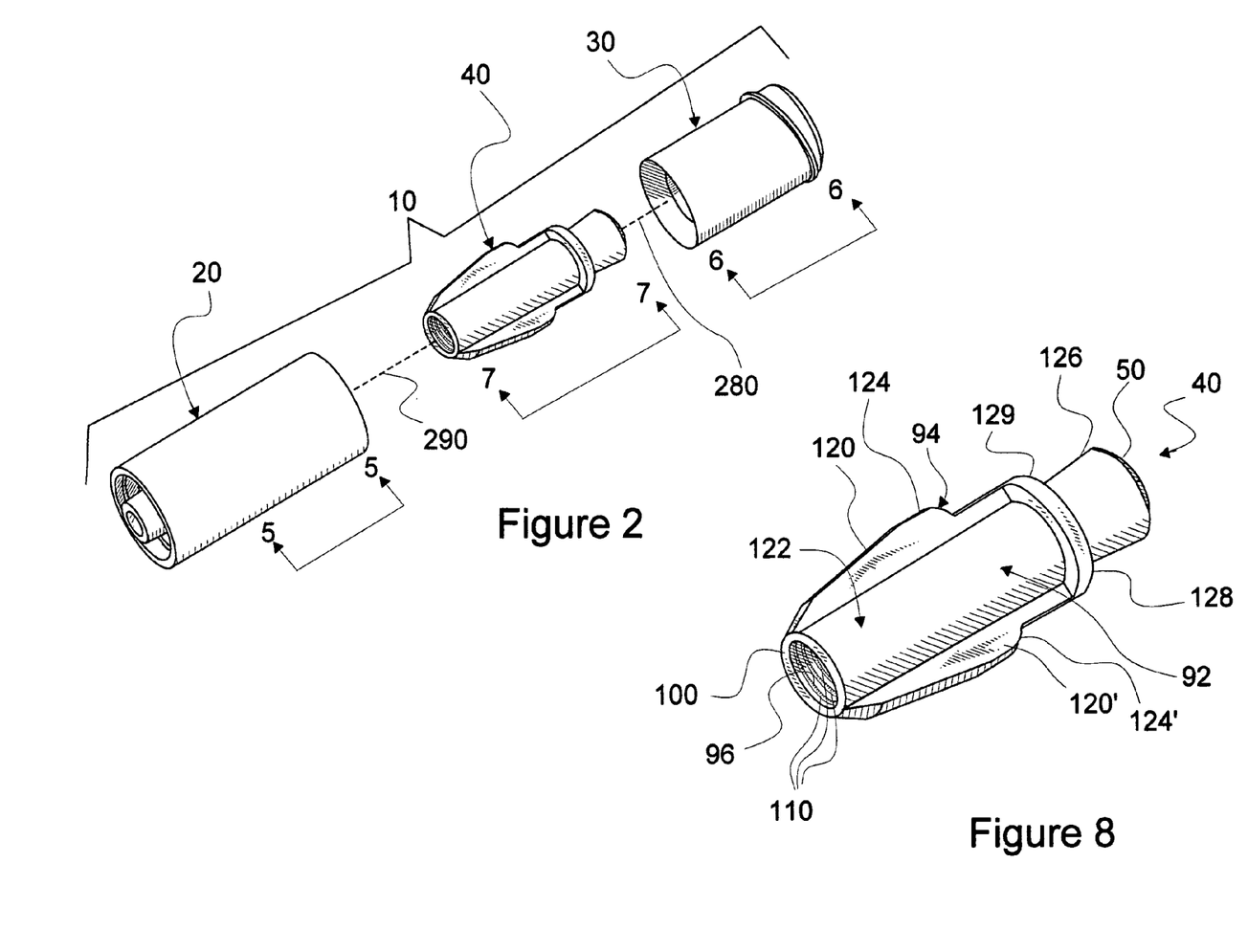
FIG. 2 is an exploded view of the needle-free connector seen in FIG. 1.
FIG. 8 is a perspective of the displaceable component seen in FIG. 2.

As seen in FIG. 1, needle-free connector 10 according to the present invention is generally made from three parts, a line or catheter communicating section 20, a male luer accessible section 30 and a displaceable component 40 where a domed valve portion 50 is seen extending outward from section 30. Section 30 is securely affixed to section 20 by adhesion, ultrasonic welding or other joining method as is commonly practiced in the medical manufacturing industry to form a housing 52 for component 40. On an end 60 distal from valve portion 50, section 20 comprises a fitting for securely affixing connector 10 to a communicating port (e.g. a male lure fitting as seen in FIG. 2). Such fittings may include, but are not limited to, "Y" connection fittings and male luer fittings.

On the end proximal to portion 50, section 30 may comprise a threaded element 70 which is sized and shaped for securing a mating luer fitting, such as that of a conventional male syringe with a complementary luer lock. Note that valve portion 50 has a slit 80 disposed across a facing surface 90 thereof. Component 10 is seen in exploded format in FIG. 2 such that sections 20 and 30 and component 40 are better seen.

Figure 7:
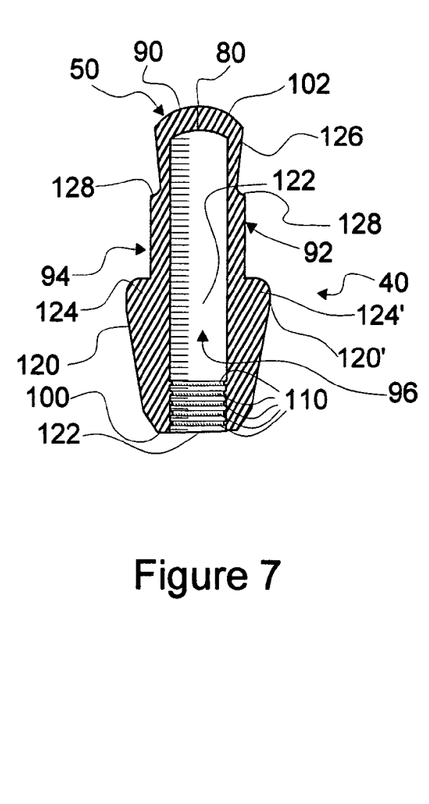
FIG. 7 is a cross section of a part taken along lines 7-7 as seen apart in FIG. 2.

Component 40 is seen, as initially molded or otherwise, formed in FIGS. 2, 7 and 8. Component 40 may be compression molded from butyl rubber. Durometer of material should be selected to provide desired elasticity, resistance to longitudinal distortion during displacement, but sufficiently supple for a luer fitting portion (as disclosed in detail hereafter) to be facilely and returnably displaced to an initial state. A durometer of 50 is presently preferred.

Component 40 has a body 92 having a somewhat irregular and uneven outer surface 94 and a smooth substantially constant diameter hollow interior surface 96 (see FIG. 7). Surface 96 is open at an end 100 opposite an end 102 which is associated with slit 80. Further, surface 96, near end 100, may be interrupted by a plurality of annular ridges, generally numbered 110. Ridges 110 are sized and shaped to provide a wiping action as surface 96 is displaced about a post disposed in section 20 (as disclosed in detail hereafter).

A pair of juxtaposed ribs 120 and 120' which are sized and shaped to communicate forces applied to surface 90 toward end 100 while deterring buckling or other folding or puckering of body 92 as component 40 is displaced within connector 10. Disposed between ribs 120 and 120' are thinned sections, generally numbered 122, which are more readily stretched than sections of body 92 associated with ribs 120 and 120'. Note that each rib 120 and 120' is substantially thickened about an arcuate region 124 and 124', respectively, purposes which are fully clarified hereafter.

Portion 50 of body 92, has an exterior side 126 which is sized and shaped to snugly fill an associated segment of a female luer fitting. Form and function of other portions of body 92 are also disclosed in more detail hereafter. Opposing end 100, portion 50 ends at a ring segment 128. At ring segment 128, distal from portion 50, ribs 120 and 120' are abruptly formed. So formed ring segment 128 provides a stop at a surface 129, see FIG. 8, to retard further displacement within section 30, in direction of portion 50, of component 40.

Figure 6:
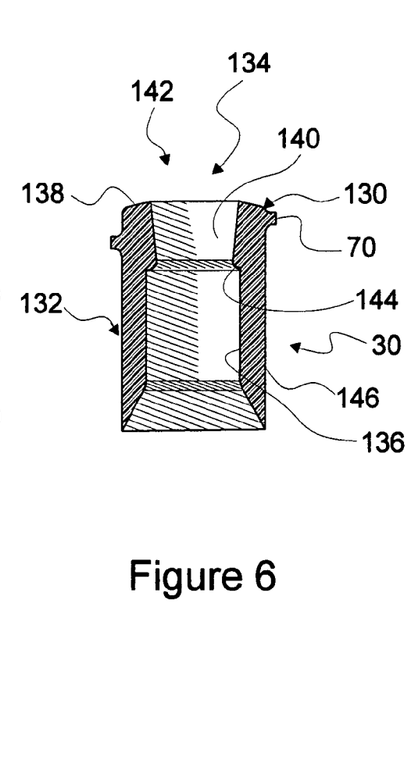
FIG. 6 is a cross section of a part taken along lines 6-6 as seen apart in FIG. 2.

Section 30, as seen in cross section in FIG. 6, has a body 130 having an arcuate substantially constant diameter exterior surface 132 (with the exception of element 70). Internally, section 30 has a hollow, cylindrical through hole 134 circumscribed by a surface 136 which varies in diameter to perform a plurality of functions along the length thereof. At an end 138 associated with exterior side 126 of body 92, a portion 140 has a luer shaped opening 142 which is sized and shaped to conform to requirements for interfacing with a male luer fitting. In this manner, opening 142 accepts and closes about side 126 of portion 50 (of component 40) when portion 50 is disposed therein (see FIG. 3). Away from portion 140, surface 136 increases in diameter to form a stop surface 144 which cooperates with stop ring 128 to limit travel distance of component 40 outward through opening 142.

Figure 3:
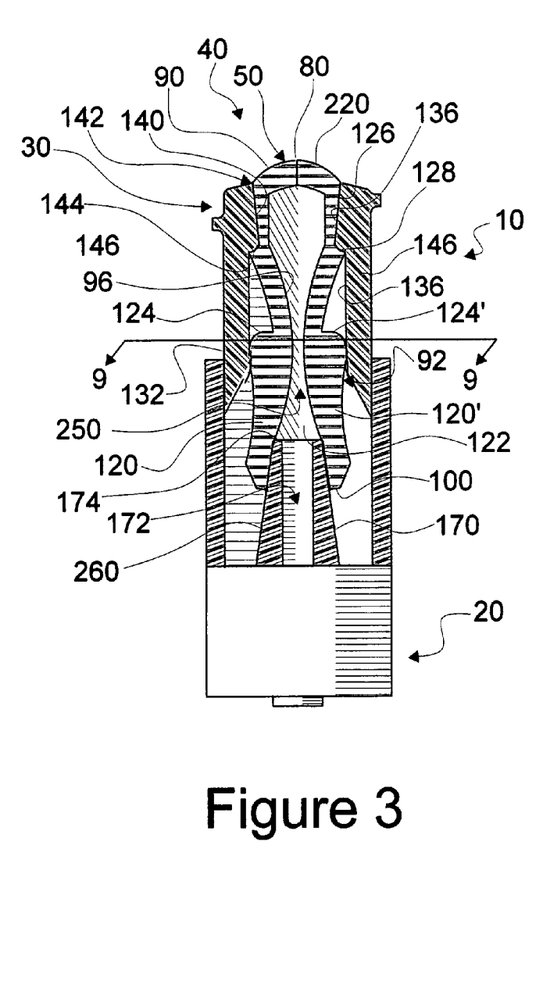
FIG. 3 is a cross section of the needle-free connector taken along lines 3-3, seen in FIG. 1.

Further along, surface 136 and exterior surface 132 define thickness of a wall 146 which in cooperation with ribs 120 and 120' distorts body 92 to significantly decrease internal volume of body 92 when regions 124 and 124' are disposed against surface 136 within wall 146, as seen in FIG. 3.

Figure 5:
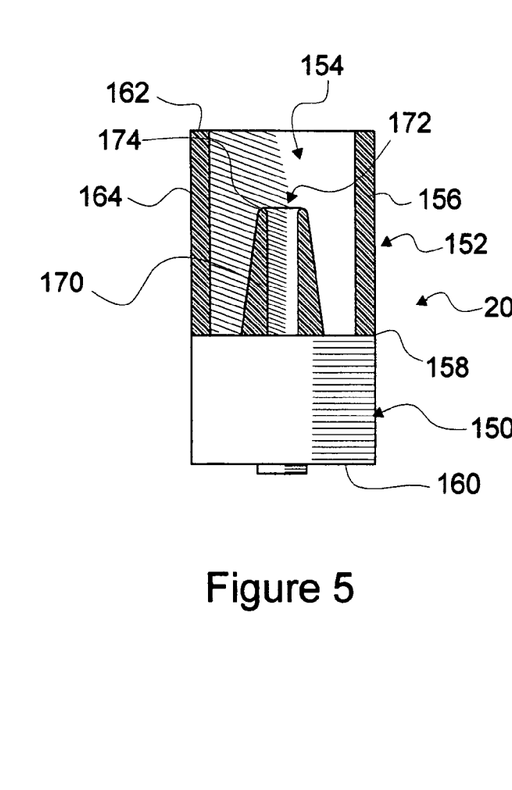
FIG. 5 is a cross section of a part taken along lines 5-5 as seen apart in FIG. 2.

Section 20, seen in cross section in FIG. 5, has a male luer-lock fitting 150 adjoined to a section 30 communicating portion 152. Portion 152 has a cylindrical well 154 with a wall 156 which interconnects to fitting 150 on one end 158 and to section 20 on the other end 162. Wall 156 circumscribes a hollow cylinder 164 which forms a portion of housing 52. Interconnections between parts, such as section 20 and section 30 are well known in medical device art and will therefore not be dealt with further herein, other than to signify that sections 20 and 30 are permanently affixed one to the other to from housing 52 for component 40.

In addition, section 20 has a medially disposed, circular post 170 which has a through hole 172 for communicating fluid to luer fitting 150. At the most distal inwardly projected end 174, post 170 is sized and shaped for being inserted into section 122 at end 100 of component 40 (see FIGS. 3 and 7) and elastically stretching thinned section 122 to form a seal about post 170, thereby. It is for this purpose that ridges 110 are disposed within surface 96 to provide a more positive seal.

Figure 4:
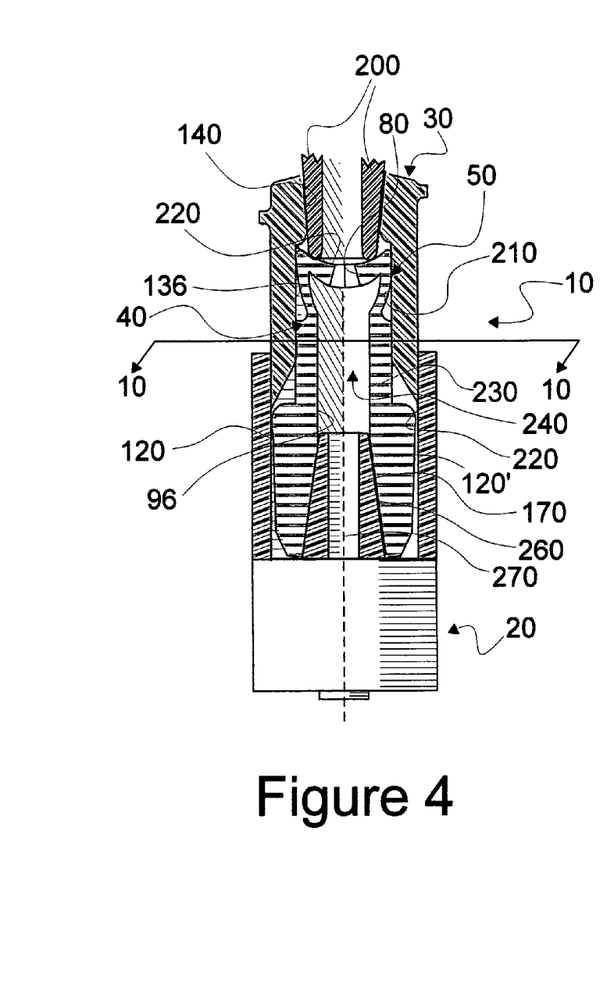
FIG. 4 is a cross section of the needle-free connector seen in FIG. 3 with a cannula inserted therein to displace an internal component to open a valve in the connector for fluid communication there through and concurrently store energy within the displaceable component, as the component is further displaced about a post, for returning the component to the position seen in FIG. 3 when the cannula is fully disengaged.

Reference is now made to FIGS. 3 and 4. In FIG. 3, displaceable component 40 is disposed such that side 126 snugly fits into portion 140 with slit 80 being in a closed state. Note that surface 136 of portion 140 provides clinching containment against exterior side 126 to forcibly retain slit 80 in the closed state. Interiorly, hollow cylindrical surface 96 is seen to vary (be narrowed) in diameter along the length thereof. This narrowing is the result of interaction between enlarged arcuate regions 124 and 124' of each rib 120 and 120', respectively, and thickened interior wall 146 of section 30.

A sealed pathway from interior surface 96 and through hole 172 is formed between component 40 at end 100 and inwardly projected end 174 by insertion of post 170 into sealing contact with thinned sections 122. On end 100 of component 40, surface 96 may have a plurality of raised circular ridges 110, as seen in FIG. 7, but not seen in FIGS. 3 and 4. Though five such ridges are seen in FIG. 7, the number of ridges may vary, dependent upon physical characteristics of material used in connector 10.

As seen in FIG. 4, a cannula 200 (seen only in part) is inserted into portion 140 to displace component 40 out of portion 140. Such displacement drives portion 50 into a widened cross section 210 of surface 136 where a dome structure 220 of domed valve portion 50 is subsequently inverted from a convex state (see FIG. 3) to a concave state to open slit 80, thereby. Opening of slit 80 provides a pathway permissive to bidirectional fluid flow through connector 10.

As disclosed supra, valve portion 50 is domed and surface 90 therefore is convex in a single stable state (see FIG. 3). Portion 50 should be specifically designed to have a single stable state which is the state seen in FIGS. 1 and 3. The enlarged diameter of cross section 210 (see FIG. 4) provides for expansion of portion 50 when an inserted cannula valve potion 50 from retainment in portion 140 Inserting a cannula (such as cannula 200 seen in FIG. 3), causes the dome of valve portion to invert (to a concave state) and slit 80 of valve portion 50 to part when portion 50 is free from fitting portion 140 defined by luer shaped opening 142 (see FIG. 6). Parting of slit 80 provides an open pathway for fluid communication there through.

In addition, displacement of component 40 relocates ribs 120 and 120' into a widened area 220 associated with section 20. Thereat, ribs 120 and 120' no longer compress surface 96 and portion 230 of component 40 is permitted to return more closely to an original (as molded) state. This state provides a space 240 which is larger than a more restricted space 250 (see FIG. 3) which is enclosed by a compressed wall of surface 92 in the state of component 40 seen in FIG. 3.

As well, the displacement of component 40 drives surface 96 still further upon post 170, increasing stretching of thinned section 122. Such stretching increases compressive elastic force against post 170. That compressive elastic force is generally resolved into force to repel component 40 to the state seen in FIG. 3 and a retaining force due to friction.

To appreciate a desired and necessary shape for a post, such as post 170, it is important to understand the scope of performance of such a post in the present invention. Using post 170 as an example, it should first be noted that component 40 has sufficient length between stop ring 128 (see FIG. 7) and end 100 to be compressively engaged about post 170 to form a sealing interface between surface 96 and post 170. Note that there is an unrelieved force due to the engagement which would force part 40 outward through opening fitting position 140 were it not for stop surface 128 (and surface 144). This unrelieved force is created by the length of part 40 between stop surface 128 and end 100. The unrelieved force causes elastic stretching of thinned sections 122 about post 170, placing pressure upon surface 96 and those ribs (110) which are in contact with surface post 170.

Such pressure is generally applied in a plane which is parallel to a plane defined by a rib 110 and resolved into two components upon an exterior surface 260 of post 170 A first component is force orthogonally applied against surface 260. A second component is force applied along or parallel to surface 260. Note, that the first or orthogonal force is a sealing force. The second or parallel force is related to potential energy for displacing part 40 off post 170. Thus, the greater the amount of stretch in thinned sections 122, the greater the potential energy for displacement.

The orthogonal force is not only a sealing force, but also in combination with a coefficient of friction between surface 260 and contacting surface of part 40 (e.g. ribs 110) results in a force which retards displacement of part 40 along surface 260. Thus, displacement force $f_d$ may be calculated as:

$$f_d = f_p - k^* f_o$$

Where:
$f_p$ is the displacing force parallel to surface of post 170
$f_o$ is the orthogonal force applied by stretching of thinned sections 122 and k is the coefficient of friction between surface 260 and contacting surface of part 40

It should be noted that, if $f_d$ is zero or negative, part 40 will not be forcibly displaced along surface 260. Also, if the coefficient of friction is zero (or small relative to orthogonal and parallel forces), displacement of part 40 along surface 260 is facilely achieved. For this reason, it is preferred that part 20 be injection molded using a synthetic resinous material which provides a "slick" surface, such as may be achieved with polypropylene. In addition, it is recommended that surface 260 be treated with a material, such as silicone, to reduce the coefficient of friction.

Of course, the parallel force may be varied by changing the slope of the cone. The greater the slope, the greater the effective displacement force per unit displacement by an inserted cannula. However, the greater the slope, the greater the elastic stretching of material in part 40. For this reason, the elastic characteristics of material used in part 40 must be considered. The amount of stretching required of the material should not exceed the elastic limit of the material. For these reasons, a moderate slope (e.g. 15° from a medial longitudinal axis as represented by dashed line 270 in FIG. 4) with emphasis upon minimizing the coefficient of friction is recommended.

Figure 11:
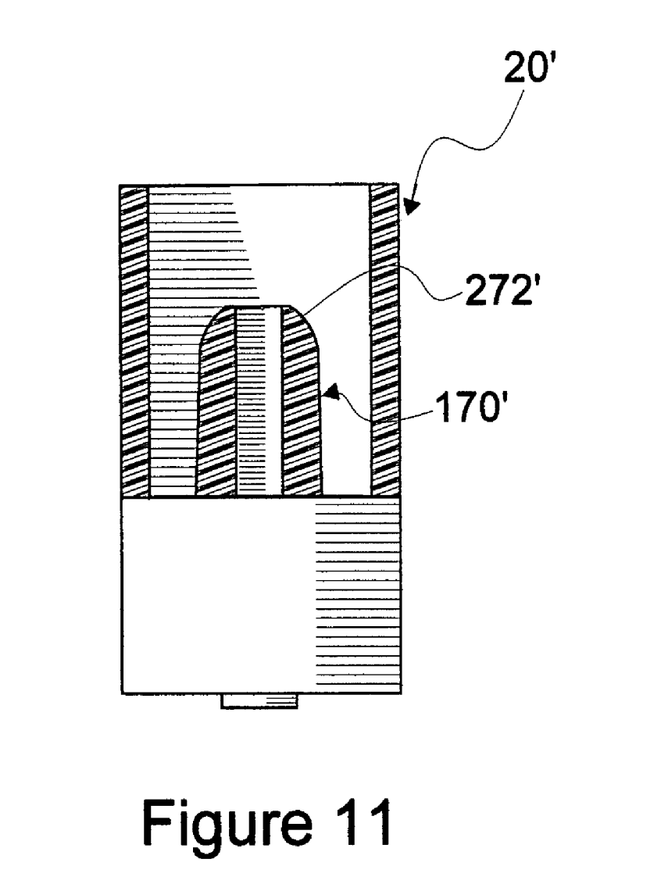
FIG. 11 is a cross section of the part seen in FIG. 5 with a conical post replaced by a post having a parabolic shape.

While post 170 is seen to be a frustum shape, it is important to note that another shape for a post may be used. For example another post 170', which may be used in the present invention, may be parabolic in shape as seen in FIG. 11. For a post, such as post 170', a parabolic shape provides a rapid change in cross sectional diameter near a tip 272' and less rapid change along post 170' away from tip 272'. In this manner, stretching of thinned section 122 may be less per unit displacement than displacement along a frustrum-shaped post 170.

Figure 12:
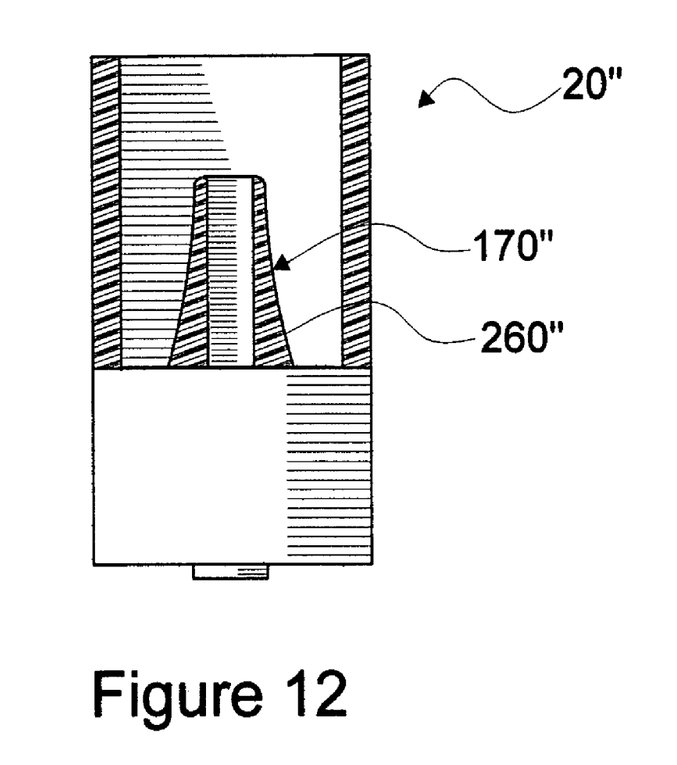
FIG. 12 is a cross section of the part seen in FIG. 5 with a conical post replaced by a post having a concave funnel shape.

Another shape for a post 170" is seen in FIG. 12. As it may be desired to make the frictional force relatively constant as thinned section is stretched along a post, post 270" has a concave shape which reduces the effective orthogonal force applied to surface 260" per unit of displacement along post 170" when compared to post 170.

Of course, another set of forces which retard displacement of component 40 from the state seen in FIG. 4 to the state seen in FIG. 3 must be considered. As mentioned supra, valve portion 50 must be sufficiently supple to be reasonably forced into fitting portion 140 for return to the state seen in FIG. 3. In addition, there must be sufficient energy (force) available to compress surface 96 to a state of more constricted volume, as also is seen in FIG. 3. Representing these two return repulsing forces by the term $f_r$, the equation for total energy, $f_t$ may be calculated as:

$$f_t = f_d - f_r = f_p - k^* f_o - f_r$$

Figure 9:
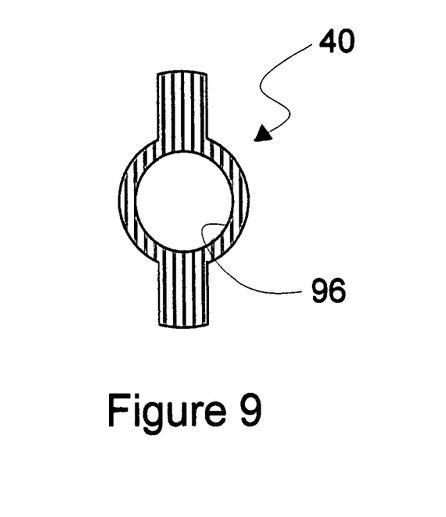
FIG. 9 is a cross section of the component taken along lines 9-9 as seen in FIG. 3.
Figure 10:
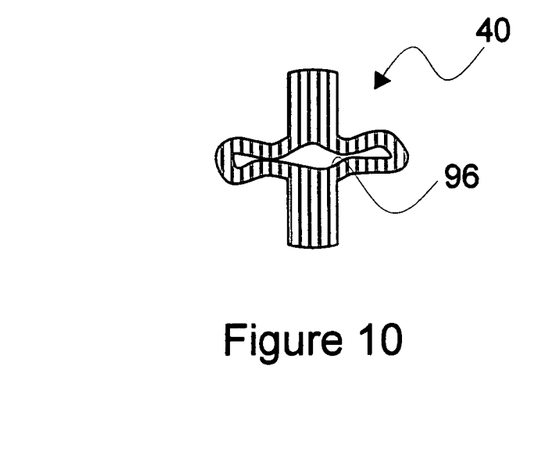
FIG. 10 is a cross section of the component taken along lines 10-10 in FIG. 4.

Relative compression to restrict volume contained within a portion of surface 96 is seen in cross section in FIGS. 9 and 10. As seen in FIG. 9, surface 96 is relatively uncompressed (or approximates initial molded condition) when in state slit 80 is in the open state. However, surface 96 is severely compressed when slit 80 is closed and portion 50 is returned to the state seen in FIG. 10. In this manner, a larger volume is contained within surface 96 in the valve open state than in the valve closed state providing a positive pressure and resulting volumetric outflow (against refluxive flow) as the state of component 40 changes from the state seen in FIG. 4 to the state seen in FIG. 3.

As seen in FIG. 2, assembly of connector 10 is preferably accomplished by inserting component 40, in a direction along dashed line 280, in to section 30 until portion 50 is disposed as seen in FIG. 1. Section 10 is then displaced in a direction defined by dashed line 290 until post 170 is sealably affixed within surface 96 and component 40 is compressed as seen in FIG. 3. Section 20 is then securely affixed to section 30 to complete the assembly. It is important to note that it is preferable for all parts to be able to be sterilized after assembly. Such sterilizing may be performed by radiation.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A connector providing a needleless connection for controllably permitting fluid communication through a passageway disposed therein, said connector comprising:

an elongated hollow housing comprising a first part and a second part securely affixed together about a medially disposed longitudinal axis, the first part having an externally communicating port being adapted to receive a blunt cannula and the second part having a port adapted for communication from the passageway to a conduit externally affixed to the second port;

a displaceable valved component disposed within the housing, said displaceable valved component comprising a valve disposed to be associated with the port of the first part, said valve being closed when the displaceable component is in a first position and forcibly opened by contact of the blunt cannula when the displaceable component is displaced to a second position;

said second part further comprising a hollow post projected inwardly into the hollow housing from the port of the second part, said hollow post comprising a through hole which communicates with the port of the second part on one end and the passageway on the other end and further comprising an external surface which decreases in radial dimension relative to the medial axis along the inward projection;

said displaceable valved component further comprising a hollow elongated tubular body which is substantially rigid lengthwise but radially elastic, said body having a length which extends, in the first position, from said first port on one end to an elastically expandable portion on the opposite end which sealingly embraces a proximally disposed portion of the post when said component is in the first position such that the passageway is closed and sealed when the component is in the first position, said expandable portion being further elastically expanded to embrace a greater proximally disposed portion of the post when the displaceable component is in the second position; and said external surface and said body comprising an associated coefficient of friction such that in combination with radial force exerted by the elastically expanded portion of the body causes the displaceable component to be displaced from the second position to the first position when the blunt cannula is displaced from contact against the displaceable component.

2. The connector according to claim 1 wherein said valved component comprises a slit valve.

3. The connector according to claim 1 wherein said valved component comprises a dome valve.

4. The connector according to claim 1 wherein said body comprises a plurality of thickened longitudinal ribs to enhance lengthwise rigidity.

5. The connector according to claim 1 wherein said post comprises a surface having a frustrum shape.

6. The connector according to claim 1 wherein said hollow elongated body comprises molded butyl rubber.

7. The connector according to claim 1 wherein said hollow elongated body comprises a plurality of radially disposed ribs for contacting said post surface.

8. The connector according to claim 1 wherein said hollow elongated body and housing in combination comprise a first stop to deter undesired displacement of the body of said displaceable component toward the port of the first part.

9. The connector according to claim 1 wherein said hollow elongated body and housing in combination comprise a second stop which determines maximum displacement of the displaceable component by insertion of a cannula into the port of the first part.

10. The connector according to claim 1 wherein said second stop comprises a position relative to a tip of a cannula and the valve which fixes the second position of the valve of the displaceable valved component for activation by the cannula.

11. The connector according to claim 1 wherein said body comprises an arcuate shape which is displaced at the second position by the post to increase inside fluid volume of the body to a greater volume than that of the body at the first position to thereby assure that fluid flow is outward from the body as the component is displaced from the second to the first position.

* * * * *